US 9,186,455 B2

(12) United States Patent
Moyer

(10) Patent No.: US 9,186,455 B2
(45) Date of Patent: Nov. 17, 2015

(54) PORT ACCESS DEVICE

(75) Inventor: Robert Moyer, Walnutport, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 2584 days.

(21) Appl. No.: 11/355,095

(22) Filed: Feb. 14, 2006

(65) Prior Publication Data

US 2007/0191771 A1    Aug. 16, 2007

(51) Int. Cl.
*A61M 5/32*    (2006.01)
*A61M 5/158*    (2006.01)
*A61M 39/02*    (2006.01)

(52) U.S. Cl.
CPC .............. *A61M 5/158* (2013.01); *A61M 39/02* (2013.01); *A61M 5/3273* (2013.01); *A61M 2005/1581* (2013.01); *A61M 2005/1587* (2013.01); *A61M 2005/325* (2013.01)

(58) Field of Classification Search
CPC .............. A61M 5/162; A61M 5/158; A61M 2005/158; A61M 2005/1587; A61M 2005/1581; A61M 39/04; A61M 39/0247; A61M 39/0208; A61M 2005/325; A61M 5/3273
USPC .............. 604/158, 93.01, 117, 161, 164.01, 604/164.04, 288.01, 165.01, 164.07, 110, 604/891.1, 192, 263; 128/919
See application file for complete search history.

(56) References Cited

U.S. PATENT DOCUMENTS

| | | | | |
|---|---|---|---|---|
| 4,531,937 | A * | 7/1985 | Yates | 604/539 |
| 4,994,041 | A * | 2/1991 | Dombrowski et al. | 604/192 |
| 5,088,984 | A * | 2/1992 | Fields | 604/167.02 |
| 5,558,651 | A | 9/1996 | Crawford et al. | |
| 5,601,536 | A | 2/1997 | Crawford et al. | |
| 6,595,954 | B1 * | 7/2003 | Luther et al. | 604/110 |
| 6,638,252 | B2 * | 10/2003 | Moulton et al. | 604/164.01 |
| 6,749,588 | B1 | 6/2004 | Howell et al. | |
| 6,764,468 | B1 * | 7/2004 | East | 604/192 |
| 7,494,481 | B2 * | 2/2009 | Moberg et al. | 604/174 |

(Continued)

FOREIGN PATENT DOCUMENTS

FR    2 867 082 A1    9/2005

OTHER PUBLICATIONS

PCT International Search Report completed Aug. 13, 2007 and mailed Oct. 1, 2007 from corresponding PCT Application No. PCT/US07/00251 filed Jan. 5, 2007 (2 pages).

(Continued)

*Primary Examiner* — Matthew F Desanto
(74) *Attorney, Agent, or Firm* — Klein, O'Neill & Singh, LLP

(57) ABSTRACT

A venous access device is generally discussed herein with particular discussions extended to port access device having a protective clip. The port access device includes a needle hub having a needle extending therefrom and a catheter hub having a catheter tube extending therefrom with the needle positioned inside the tube in a ready to use position. A tip protector is positioned inside a clip housing, which is positioned in between the catheter hub and the needle hub.

35 Claims, 3 Drawing Sheets

(56) References Cited

U.S. PATENT DOCUMENTS

| | | |
|---|---|---|
| 2002/0095138 A1 | 7/2002 | Lynch et al. |
| 2002/0169418 A1* | 11/2002 | Menzi et al. ............. 604/164.07 |
| 2003/0158520 A1 | 8/2003 | Safabash et al. |
| 2004/0116856 A1* | 6/2004 | Woehr et al. .................. 604/110 |
| 2004/0158207 A1 | 8/2004 | Hunn et al. |
| 2004/0162518 A1 | 8/2004 | Connelly et al. |
| 2005/0101910 A1* | 5/2005 | Bowman et al. ........... 604/93.01 |
| 2005/0101912 A1 | 5/2005 | Faust et al. |
| 2005/0182363 A1* | 8/2005 | Kulli .............................. 604/110 |
| 2005/0267441 A1 | 12/2005 | Douglas |
| 2006/0253076 A1* | 11/2006 | Butts et al. ............... 604/167.06 |
| 2007/0038188 A1* | 2/2007 | Bialecki et al. .......... 604/164.08 |
| 2007/0073222 A1* | 3/2007 | Lilley et al. ................... 604/110 |

OTHER PUBLICATIONS

PCT Written Opinion of the International Searching Authority completed Aug. 13, 2007 and mailed Oct. 1, 2007 from corresponding PCT Application No. PCT/US07/00251 filed Jan. 5, 2007 (6 pages).

Notification of Transmittal of International Preliminary Report on Patentability completed May 15, 2009 and mailed Jun. 16, 2009 from corresponding PCT Application No. PCT/US07/00251, filed Jan. 5, 2007 (7 pages).

Extended European Search Report dated Oct. 14, 2014 from corresponding European Application No. 07716348.3 (8 pages).

* cited by examiner

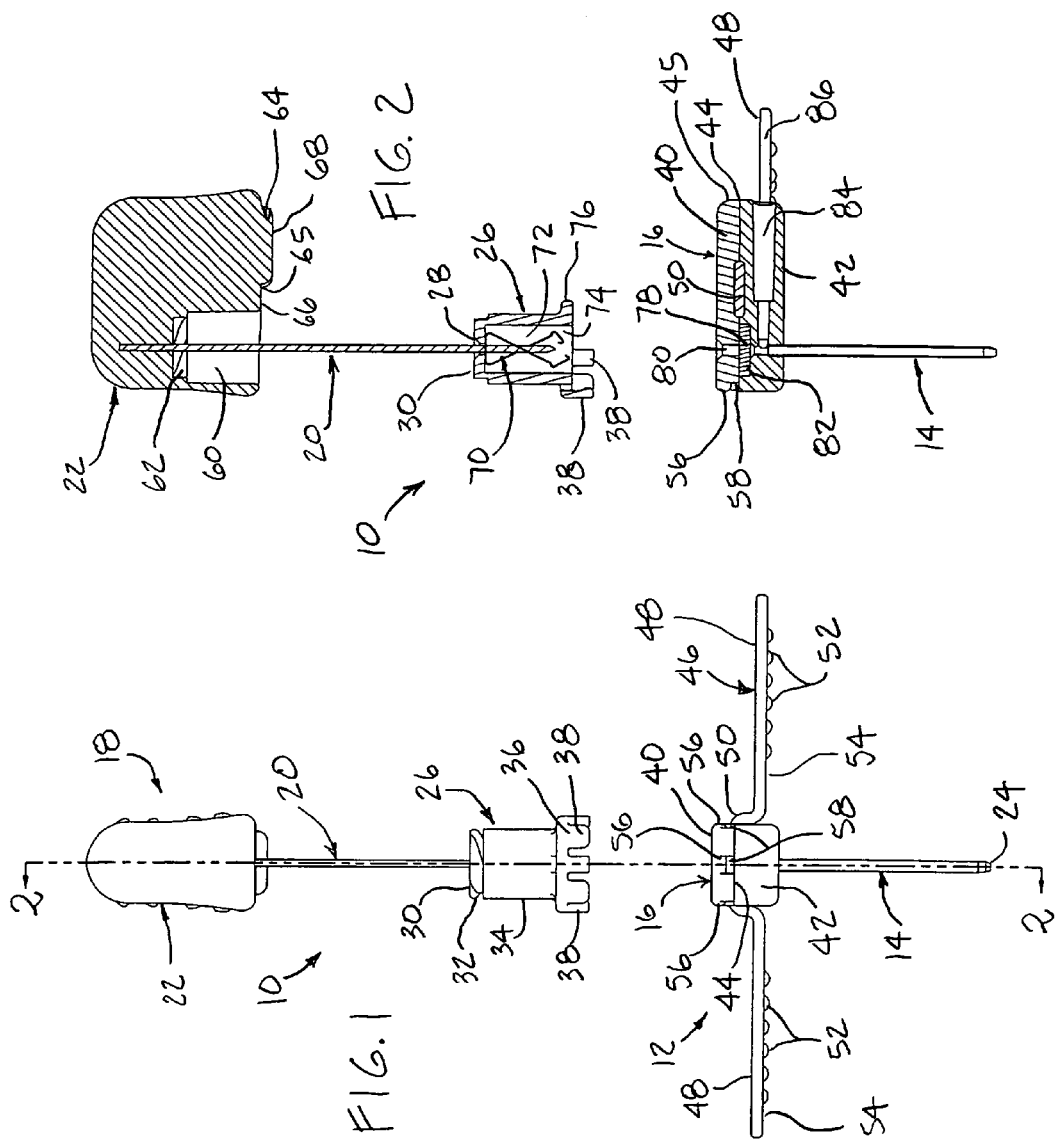

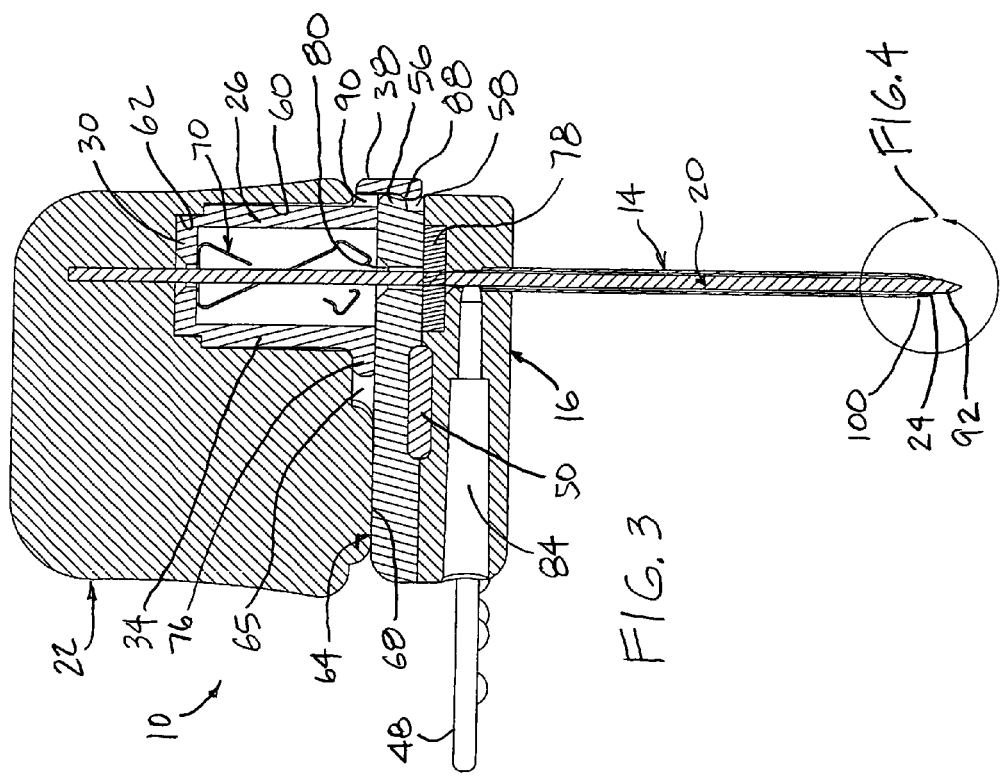

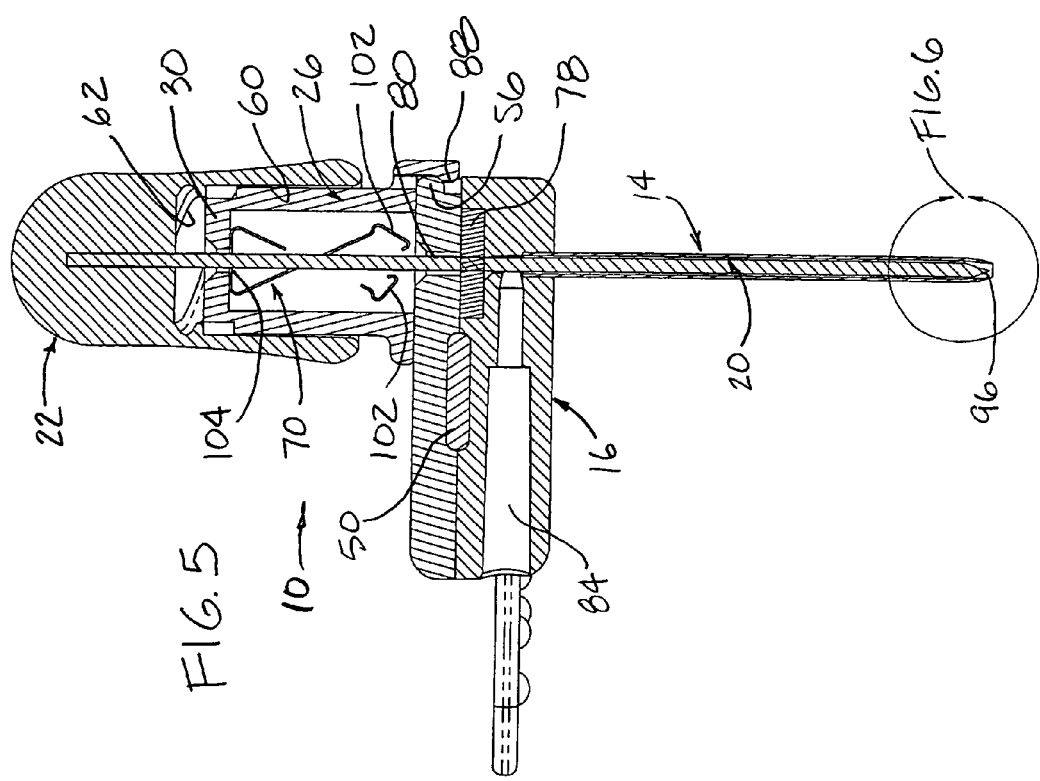

PORT ACCESS DEVICE

A venous access device is generally discussed herein with particular discussions extended to port access device having a protective clip.

BACKGROUND

Venous access to a patient's venous system may be accomplished using a peripheral intravenous catheter (PIC) in some instances and a central venous catheter (CVC) in other instances, which are well known in the health care industry. For long term venous access, a subcutaneous implantable port (sometimes referred to only as "port") is preferred. An implantable port generally comprises an injection port housing, typically made from an exotic metal such as titanium, and a catheter implanted under the skin with a catheter connected.

To access a patient's venous system, a Huber needle is typically used to puncture through the injection port housing, and obviously through the skin. Once completed, the injection port housing reseals itself. It is not uncommon to be able to access the injection port housing hundreds of times before having to replace it. It is also not uncommon to leave a Huber needle in the injection port housing for extended time periods, in the order of several days, without increased complications. However, the longer the needle remains in the port, the more difficult it is to remove. It is well documented that this resistance to removal causes a rebound affect when the needle is withdrawn from the port thus resulting in possible needle sticks to the clinician. In addition, the rigid needle remains in a layer of tissue directly above the port resulting in discomfort to the patient.

More recently, the use of a polymer, such as a polyurethane catheter, to access the injection port housing is preferred as it increases the intervals between having to remove the device from the injection port housing, and hence the number of punctures through the same housing for venous access. It would be desirable to use a plastic catheter over a needle for port access. That way, the needle can be withdrawn immediately after insertion leaving only the plastic catheter in place. The flexible (or semi-rigid) catheter would provide more comfort to the patient and be easier to remove. It would also be desirable to provide a safety shield to protect the needle point after removal to prevent inadvertent sticks.

SUMMARY

The present invention may be implemented by providing an access port device comprising a catheter hub comprising a catheter tube extending therefrom, a needle hub comprising a needle having a needle tip extending through the catheter tube, and a housing disposed between the needle hub and the catheter hub; the housing being engaged to the catheter hub so that when the needle hub is rotated relative to the housing, the housing remains fixed to the catheter hub.

In another aspect of the present invention, there is provided an access port device comprising a catheter hub comprising a catheter tube extending therefrom, a needle hub comprising a needle having a needle tip extending through the catheter tube and beyond a distal end of the catheter tube, a housing disposed between the needle hub and the catheter hub, and a tip protector for covering the needle tip positioned inside a cavity defined by the housing; wherein the housing is threadedly engaged to the needle hub.

In yet another aspect of the present invention, there is provided An access port device comprising a catheter hub comprising a catheter tube extending therefrom, a needle hub comprising a needle having a needle tip extending through the catheter tube and beyond a distal opening of the catheter tube, a housing disposed between the needle hub and the catheter hub, and a tip protector for covering the needle tip positioned inside a cavity defined by the housing; wherein the catheter hub further comprises a flow chamber in fluid communication with the catheter tube.

Other aspects of the present invention includes provisions for controllably rotating a needle hub a desired rotation and moving a needle an axial length relative to a catheter tube.

In yet other aspects of the present invention, an access port device is provided whereby a pair of wing flaps extend radially outwardly from a catheter hub for resting against a patient's skin.

In other aspects of the present invention, an access port device is provided in which a needle is a solid metallic stylus.

In yet another aspect of the present invention, an access port device is provided in which a septum is incorporated in a catheter hub for occluding a needle port through the hub.

These and other features and advantages of the present invention will become appreciated as the same become better understood with reference to the specification, claims and appended drawings.

BRIEF DESCRIPTION OF THE DRAWINGS

The drawings appended herein include:

FIG. 1 is a semi-schematic exploded side view of a port access device provided in accordance with aspects of the present invention;

FIG. 2 is a semi-schematic cross-sectional side view of the device of FIG. 1 taken along line 2-2;

FIG. 3 is a semi-schematic cross-sectional side view of the device of FIG. 1 in a ready to use-position;

FIG. 4 is an enlarged cross-sectional view of the needle tip of FIG. 3;

FIG. 5 is a semi-schematic cross-sectional side view of the device of FIG. 3 with the needle hub rotated relative to the catheter hub; and FIG. 6 is an enlarged cross-sectional side view of the needle tip of FIG. 5.

DETAILED DESCRIPTION

The detailed description set forth below in connection with the appended drawings is intended as a description of the presently preferred embodiments of a port access device provided in accordance with aspects of the present invention and is not intended to represent the only forms in which the present invention may be constructed or utilized. The description sets forth the features and the steps for constructing and using various embodiments of the port access device of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Referring now to FIG. 1, a semi-schematic exploded side view of a port access device provided in accordance with aspects of the present invention is shown, which is generally designated 10. In one exemplary embodiment, the port access device 10 comprises a winged catheter 12, which comprises a catheter tube 14 attached to and extending from a catheter hub 16, and a needle assembly 18, which comprises a needle 20 attached to and extending from a needle hub 22. In use, the needle assembly 18 is normally coupled to the winged catheter 12 with the needle 20 projecting through the catheter tube 14 and the tip of the needle exposed through the distal end opening 24 of the catheter tube.

In one exemplary embodiment, a housing 26 comprising a central opening 28 (FIG. 2) is incorporated and positioned between the winged catheter 12 and the needle assembly 18. The housing 26 is configured to house a protective clip for covering the tip of the needle after the needle is withdrawn from an injection port housing. As further discussed below, the housing 26 is also configured to lock from rotating against the catheter hub 16 and jack the needle hub 22 a controlled distance relative to the catheter hub 16 to create a flow path for blood flashback.

In one exemplary embodiment, the housing 26 comprises a housing top 30 comprising a plurality of threads 32, a body section 34, and a skirt section 36. The housing top 30 is configured to threadedly couple to a corresponding threaded female bore located on the needle hub 22. The threads are sized and angled so as to produce a desired lead when the needle hub 22 is rotated an arc degree relative to the housing, as further discussed below.

In one exemplary embodiment, the skirt section 36 comprises a plurality of downwardly extending teeth 38. The teeth 38 are preferably formed around the lower periphery of the body section 34. More preferably, the teeth are formed around about half of the lower periphery of the body section 34 to facilitate grabbing an upper edge of the catheter hub 16, as further discussed below. The teeth 38 are configured to interact with the upper edge of the catheter hub 16 to prevent the housing 26 from rotating relative to the catheter hub 16.

In one exemplary embodiment, the catheter hub 16 comprises an upper hub block 40 coupled to a lower hub block 42. In one application of the invention, the two hub blocks 40, 42 are bonded together along a seam 44, using high frequency welding or adhesive. As further discussed below, a septum and an attachment wing are preferably wedged in between the two blocks 40, 42 prior to bonding the two.

In one exemplary embodiment, a low profile attachment wing 46 comprising two wing flaps 48 attached to one another at a bridge 50 is incorporated. The two wing flaps 48 extend radially outwardly from the catheter hub 16 and in one exemplary embodiment lie generally on a same plane. The two wing flaps 48 may incorporate different shapes but are preferably both generally rectangular in configuration. In one exemplary embodiment, a plurality of raised bumps 52 are incorporated on an underside surface 54 of each wing flap 48. When incorporated, the raised bumps 52 allow a patient's skin to breath by providing gaps between the underside surfaces 54 of the wing flaps 48 and the skin.

In one exemplary embodiment, a plurality of male detents 56 are incorporated in the catheter hub 16. More specifically, in one exemplary embodiment, a plurality of undercuts 58 are formed on the upper hub block 40 along a lower section of the hub block, near the seam 44. The detents 56 are formed above the undercuts 58 due to the voids provided in forming the undercuts 58. As further discussed below, the combination male detents 56 and undercuts 58 are configured to interact with the teeth 38 on the clip housing 26 to inhibit relative movement between the two. In a preferred embodiment, three detents 56 and three undercuts 58 are incorporated.

Referring now to FIG. 2, a semi-schematic cross-sectional side view of the port access device of FIG. 1 is shown, taken along line 2-2. In one exemplary embodiment, the needle hub 22 incorporates a generally cylindrical bore 60 defining a cavity and having a recessed boss 62 comprising corresponding threads for mating with the threads 32 on the housing top 30 of the clip housing 26. The cylindrical bore 60 is sized to receive the clip housing 26 having a protective clip disposed therein, as further discussed below.

In one exemplary embodiment, the needle hub 22 comprises a base 66 comprising a base surface and a projection 64 that extends outwardly from the base surface. The projection 64 defines a gap 65 or elevation difference between the base surface 68 of the projection 64 and the base surface of the base 66. In one exemplary embodiment, the gap 65 comprises a dimension that approximately equals a height of a flange located on the clip housing 26, as further discussed below.

In one exemplary embodiment, the needle 20 is molded into the needle hub 22. More preferably, the needle is positioned centrally of the bore 60 when molded into the hub 22. Alternatively, a bore having a well may be incorporated into the hub and the needle 20 attached thereto using curable glue or adhesive. In one exemplary embodiment, the needle 20 comprises a 12 gauge to a 26 gauge solid metallic stylus. More preferably, the needle 20 is solid and incorporates a non-coring needle tip. In a preferred embodiment, the needle tip comprises a Trocar-type needle tip. Alternatively, a Huber-type bevel needle tip or a pencil point needle may be incorporated.

In one exemplary embodiment, a clip or needle tip protector 70 is incorporated for blocking the needle tip following a needle puncture. In one exemplary embodiment, the clip 70 is one of the types disclosed in patent application Ser. No. 10/734,931, filed Dec. 12, 2003, entitled SPRING CLIP SAFETY IV CATHETER, the contents of which are expressly incorporated herein by reference. Alternatively, the clip may be one of the types that cant over so that an opening located on the clip grips the needle when activated. Exemplary clips of the latter type are disclosed in U.S. Pat. Nos. 5,611,781, 6,406,459, and 6,709,419 and in application Ser. No. 10/905,884, filed Jan. 25, 2005; Ser. No. 10/450,809, filed Dec. 5, 2001; and Ser. No. 10/906,171, filed Feb. 5, 2005, the contents of each of which are expressly incorporated herein by reference.

In one exemplary embodiment, the clip housing 26 defines an interior cavity 72 sized to receive the tip protector 70. In a preferred embodiment, the clip housing 26 remains with the tip protector 70 following activation, such as that shown in FIG. 2, by incorporating a housing top 30 having an opening 28 formed therethrough. Alternatively, the housing top 30 may be eliminated so that following an injection, the tip protector 70 may pass through the opening where the housing top 30 would otherwise be incorporated. If the housing top 30 is eliminated, an inward projection should be incorporated in the interior cavity 72 of the clip housing 26 for retaining the tip protector 70 with the housing during movement from between a ready to use position to an activated position. The inward projection defines a section in the interior cavity 72 with a smaller diameter than the diameter of the cavity at the opening 74 of the housing, which is the same as near the housing top 30. Following activation, the clip collapses over the needle tip and has a smaller profile that enables it to pass through the projection inside the interior cavity to thereby separate from the clip housing 26.

In one exemplary embodiment, a flange 76 is incorporated on the clip housing 26, preferably at the opening 74 of the clip housing. The flange 76 is configured to project into the gap 65 at the base 66 of the needle hub 22 when the port access device 10 is in the ready to use position, as further discussed below.

As previously alluded to, the catheter hub incorporates a septum 78 for occluding the needle port 80 above the septum. The septum 78 is incorporated by providing a recessed space 82 in the lower hub block 42 for receiving the septum. Part of the needle port 80 extends below the septum 78 and is in fluid communication with the catheter tube 14. A flow chamber 84 is incorporated in the lower hub block 42 and is in fluid communication with the catheter 14. The flow chamber 84 is preferably sized to receive a tubing (not shown) and has a tapered wall for a tapered fit with the tubing. As is readily apparent to a person of ordinary skill in the art, the flow chamber 84 acts as a conduit for passing fluid flow from between the catheter tube 14 and the tubing, such as, e.g., for taking a sample from an injection site, for administration of medications, for administration of fluids, and for transfusion of blood products.

Also shown in FIG. 2 is a cross-sectional side view of the bridge 50 of the low profile wing 46, which passes through the seam 44 adjacent the septum 78. A side edge 86 of one of the wing flaps 48 is also shown. It is clear that in the embodiment shown, the wing flaps 48 comprise a length that that extends past the end 45 of the catheter hub 16.

FIG. 3 is a cross-sectional side view of the port access device 10 in a ready to use position. The device 10 is placed in the ready to use position by first engaging the housing top 30 of the clip housing 26 with the threaded recess boss 62 of the needle hub cavity 60. This is accomplished by rotating either the clip housing 26 or the needle hub 22 relative to the other. The tip protector 70 is then moved to a proximal most position inside the clip housing 26. The needle 20 is then advanced through the needle bore 80 and through the septum 78. The needle hub 22, with the clip housing 26 attached thereto, is advanced until the base 68 of the projection 64 contacts the upper surface of the catheter hub 16 and the teeth 38 on the clip housing 26 engage the detents 58 on the catheter hub 16.

In one exemplary embodiment, the teeth 38 each incorporates a lip 88 configured to positively engage the detents 56. A snug fit between the needle 20 and the septum 78 and between the lips 88 and the detents 56 firmly secures the combination needle hub 22 and clip housing 26 to the catheter hub 16. In the embodiment shown, the teeth 38 are each attached to the body section 34 of the clip housing 26 via two side walls 90 (with only one shown in the FIG. 3 cross-sectional view), which define a gap or a channel therebetween. In an alternative embodiment, the clip housing 26 incorporates a pin under the flange 76 and the catheter hub 16 a corresponding boss to prevent relative rotation. In yet another alternative embodiment, the clip housing 26 and the bore 60 may incorporate detents to control axial movement instead of threads, as further discussed below.

FIG. 4 is an enlarged view of the needle tip 92 extending past the distal end 100 of the catheter tube 14. In one exemplary embodiment, the catheter tube 14 comprises an internal diameter 96 sized about 4 mils to about 30 mils larger than the outside diameter of the needle 20, with a range of 4 mils to 12 mils being more preferred. An annular space 98 is formed due to the size difference between the internal diameter 96 of the catheter tube and the outside diameter of the needle 20. The distal end 100 of the catheter tube 14, however, is reduced so that the distal end of the catheter tube 14 has an opening 24 that is smaller in diameter than the internal diameter 96 of the tube. In a preferred embodiment, the end opening 24 is about the same size as the diameter of the needle 20. In a more preferred embodiment, the end opening is about 0.5 mil to about 1.5 mil smaller than the diameter of the needle 20. A seal or a close tolerance fit is thus formed by the relative dimensions between the end opening 24 of the catheter tube and the needle 14.

FIG. 5 is a cross-sectional side view of the access port device of FIG. 3 with the needle hub 22 rotated relative to the catheter hub 16 and the clip housing 26. In other words, the catheter hub 16 and the clip housing 26 are fixed or are substantially fixed to one another while the needle hub 22 is rotated relative to the two. In one exemplary embodiment, the needle hub 22 is rotated a quarter turn counter-clockwise to disengage the housing top 30 of the clip housing 26 from the threaded boss 62 located in the cavity 60 of the needle hub. In a preferred embodiment, the quarter turn counter-clockwise causes the hub 22 to move about 0.050 inch axially, which corresponds to a 0.050 inch lead at a quarter turn on the threads. Because the needle 20 is attached to the needle hub 22, the axial movement causes the tip 92 to move the same distance, which moves it into the lumen of the catheter tube 14.

With reference to FIG. 6 in addition to FIG. 5, the annular space 98 is exposed to the end opening 24 of the catheter tube 14. Had the port access device 10 being used on a port site and rotated as described, blood flashback would flow through the annular space 98 and the flow chamber 84 and out through the tubing (assuming one is attached to the flow chamber). Blood flashback provides an indicator that the port access device 10 is properly placed through an injection port housing of an implantable catheter. If placement of the port device 10 is satisfactory, the needle 20 may be retracted completely while leaving the catheter hub 16 and catheter tube 14 in place.

To retract the needle 20 from the catheter tube 14, the needle hub 22 is moved axially away from the catheter hub 16. Once the tip 92 moves proximally of the septum 78 and into the upper needle port chamber 80, the clip housing 26 may start to move, shift, or tilt as the combination needle and septum no longer provides an anchoring point to securely hold the clip housing 26 in place. The hub 22 is further retracted proximally until the needle tip moves just proximal of the two distal walls 102 of the tip protector 70, at which time or approximately contemporaneously thereto, the proximal opening 104 on the tip protector 70 engages a bump, crimp, deformity, or change in profile (not shown) on the needle 20. Still further proximal movement of the needle hub will lift the combination clip housing 26 and tip protector 70 away from the catheter hub 16 due to the engagement between the opening 104 on the proximal wall of the tip protector and the bump or crimp on the needle. Referring again to FIG. 2, the activated clip 70 and clip housing 26 will appear as shown when activated.

Although limited embodiments of the port access device and their components have been specifically described and illustrated herein, many modifications and variations will be apparent to those skilled in the art. For example, the shape of the catheter hub, needle hub, and/or clip housing may be modified, the plastic can be mo, etc. Furthermore, it is understood and contemplated that features specifically discussed for one valve embodiment may be adopted for inclusion with another valve embodiment, provided the functions are compatible. For example, certain curvatures and contours incorporated in one valve may be incorporated in another valve for aesthetic appeal and improved functionality, such as for improved gripping purposes. Accordingly, it is to be understood that the valve assemblies and their components constructed according to principles of this invention may be embodied other than as specifically described herein. The invention is also defined in the following claims.

What is claimed is:

1. An access port device comprising:
   a catheter hub comprising a hub body, a catheter tube having a tube opening extending from the hub body, a flow chamber defined by the hub body comprising a flow opening terminating at an exterior surface of the hub body, and a needle port having an opening terminating at the exterior surface of the hub body, which is spaced apart from the flow opening;

a needle hub having internal threads formed in the needle hub, the needle hub comprising a needle having a needle tip extending through the opening of the needle port and the catheter tube but not the flow opening of the flow chamber; and a housing disposed between the needle hub and the catheter hub; the housing being removably engaged to the catheter hub and the needle hub; the housing having external threads threadedly engaged to the internal threads of the needle hub: and wherein the tube opening is at an angle to the flow opening of the flow chamber and the needle is mounted off-center relative to the needle hub;

wherein when the needle hub is rotated relative to the housing and the catheter hub, the housing remains fixed to the catheter hub and the needle hub moves a control distance relative to the catheter hub to create a flow path for blood flashback.

2. The access port device of claim 1, wherein the catheter hub comprises a recessed space having a septum located therein.

3. The access port device of claim 2, wherein the needle passes through the septum.

4. The access port device of claim 2, wherein the septum is located between the opening of the needle port and the catheter tube.

5. The access port device of claim 1, wherein a base of the needle hub includes a projection that abuts, but does not penetrate, the catheter hub, thereby creating a gap between the needle hub and the catheter hub.

6. The access port device of claim 5, wherein the gap has a height substantially equal to a height of a flange on the housing.

7. The access port device of claim 1, wherein rotation of the needle hub relative to the housing retracts the needle proximally into the catheter tube.

8. The access port device of claim 7, wherein rotation of the needle hub relative to the housing removes a seal between the needle and the tube opening.

9. The access port device of claim 1, wherein the housing comprises a plurality of spaced apart teeth that engage exterior sections of the catheter hub.

10. The access port device of claim 1, wherein the needle is at least one of a Huber needle, a Trocar needle, and a pencil point needle.

11. The access port device of claim 1, further comprising a tip protector for covering the needle tip located inside a cavity of the housing.

12. The access port device of claim 1, wherein the catheter hub comprises two planar wings extending radially of the hub body, the wings each comprises an underside planar surface for resting against an object to be accessed and wherein the catheter tube extends generally orthogonally of the underside planar surface.

13. An access port device comprising:

a catheter hub comprising a catheter tube extending therefrom and a flow port, a needle hub having internal threads formed in the needle hub, the needle hub comprising a needle having a needle tip extending through the catheter tube and beyond a distal end of the catheter tube, a housing disposed between the needle hub and the catheter hub comprising an axial opening having the needle passing therethrough, the housing having external threads, and a tip protector for covering the needle tip when the needle is retracted away from the catheter tube positioned inside a cavity defined by the housing; and wherein the external threads of the housing threadedly engage with the internal threads formed in the needle hub; and wherein the needle hub is rotatable relative to the housing to disengage the needle hub a controlled distance relative to the catheter hub to create a flow path for blood flashback and the housing remains removably fixed to the catheter hub during rotation of the needle hub relative to the housing.

14. The access port device of claim 13, wherein a base of the needle hub includes a projection that abuts, but does not penetrate, the catheter hub, thereby creating a gap between the needle hub and the catheter hub.

15. The access port device of claim 14, wherein the gap has a height substantially equal to a height of a flange on the housing.

16. The access port device of claim 13, wherein rotation of the needle hub relative to the housing retracts the needle proximally into the catheter tube.

17. The access port device of claim 16, wherein the catheter tube has an end opening that is smaller in diameter than a diameter of the needle thereby forming a seal with the needle, and when the needle hub is rotated relative to the catheter hub, the seal is broken.

18. The access port device of claim 13, wherein the housing comprises a plurality of spaced apart teeth for engaging exterior sections of the catheter hub.

19. The access port device of claim 13, wherein the needle is at least one of a Huber needle, a Trocar needle, and a pencil point needle.

20. The access port device of claim 13, wherein the catheter hub comprises a needle port having an opening, and wherein the needle port is spaced from the flow port.

21. The access port device of claim 13, wherein needle tip moves proximally of the distal end of the catheter tube when the needle hub is rotated relative to the catheter hub.

22. The access port device of claim 13, wherein the catheter hub comprises a recessed space comprising a septum having the needle passing therethrough.

23. The access port device of claim 13, wherein the catheter hub comprises at least one wing.

24. An access port device comprising:

a catheter hub comprising a needle port having a needle inlet opening, a catheter tube, and a flow chamber having a flow inlet opening spaced from the needle inlet opening formed in the catheter hub for fluid flow through the catheter hub in fluid communication with the catheter tube;

a needle hub comprising a needle having a needle tip extending through the needle inlet opening of the needle port and the catheter tube and beyond a distal opening of the catheter tube, a housing disposed between the needle hub and the catheter hub and removably coupled to both the needle hub and the catheter hub, and a tip protector for covering the needle tip when the needle is removed from the catheter tube located inside the housing; and wherein a fluid path defined by the catheter tube is orthogonal to a fluid path defined by the flow chamber;

wherein the needle hub is threadedly engaged with the housing;

wherein the housing is configured to lock from rotating against the catheter hub, when the needle hub moves a control distance relative to the catheter hub to create a flow path for blood flashback during rotation of the needle hub with respect to the housing.

25. The access port device of claim 24, wherein the catheter hub comprises a first catheter hub stack coupled to a second catheter hub stack and having a septum disposed therein.

26. The access port device of claim 25, wherein the needle passes through the septum but not the flow inlet opening.

27. The access port device of claim 24, wherein the housing comprises exterior threads that threadedly engage internal threads formed in the needle hub.

28. The access port device of claim 27, where the needle hub is rotatable relative to the housing to separate the internal threads and exterior threads from one another.

29. The access port device of claim 24, wherein a base of the needle hub includes a projection that abuts, but does not penetrate, the catheter hub, thereby creating a gap between the needle hub and the catheter hub.

30. The access port device of claim 29, wherein the gap has a height substantially equal to a height of a flange on the housing.

31. The access port device of claim 24, wherein rotation of the needle hub relative to the housing retracts the needle proximally into the catheter tube.

32. The access port device of claim 31, wherein rotation of the needle hub relative to the housing removes a seal between the needle and the distal opening of the catheter tube.

33. The access port device of claim 24, wherein the housing comprises a plurality of teeth formed partially around a circumference of the housing.

34. The access port device of claim 24, wherein the flow inlet opening and needle inlet opening both terminate at an exterior surface of the catheter hub.

35. The access port device of claim 24, wherein the catheter hub comprises at least one wing.

* * * * *